Figure 1:
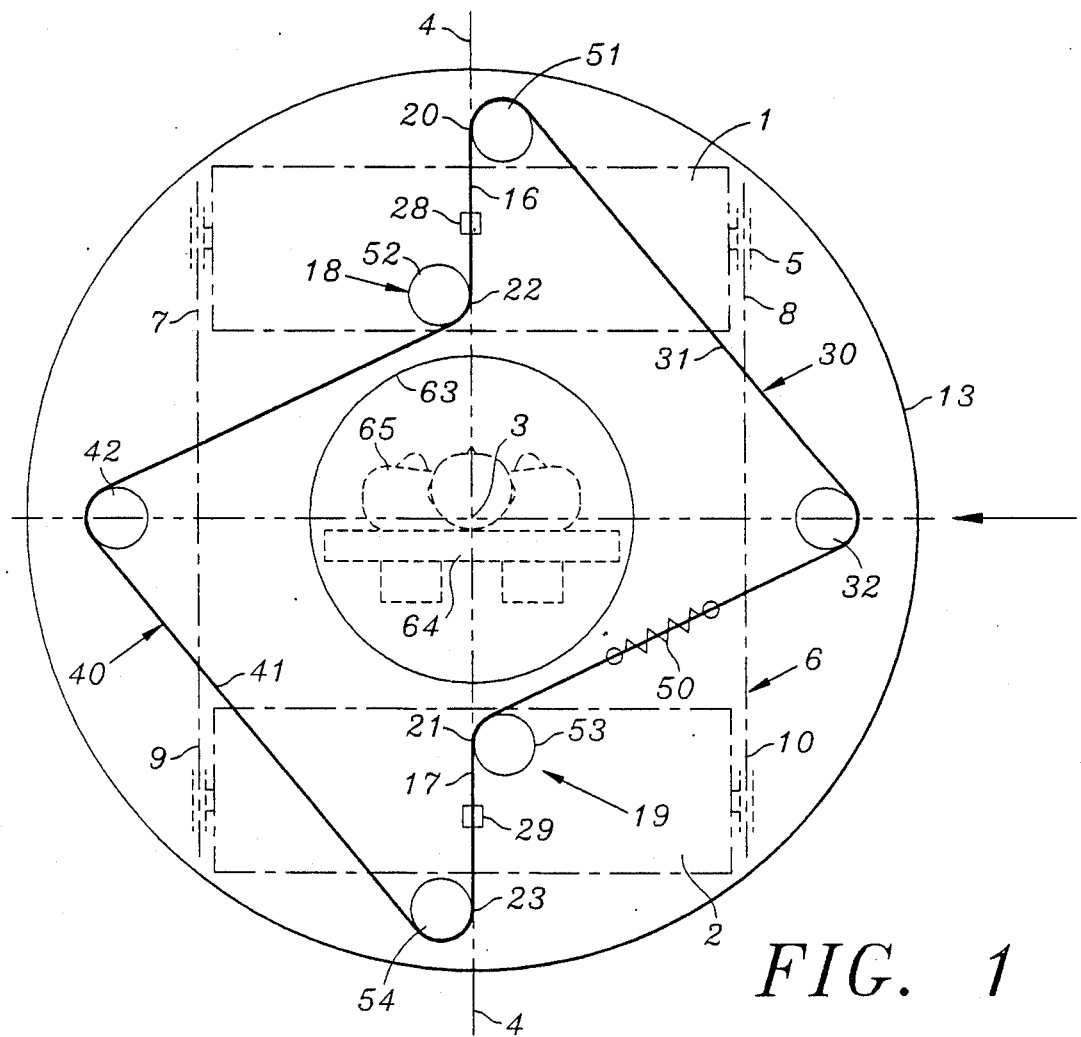

United States Patent [19]

Sanz et al.

[11] Patent Number: 5,039,859

[45] Date of Patent: Aug. 13, 1991

[54] DEVICE FOR MOVING AT LEAST TWO MASSES WITH RESPECT TO A CENTRAL AXIS OF SYMMETRY

[75] Inventors: Paul A. Sanz; Ives J. Meliciani, both of Toulouse, France

[73] Assignee: Societe Auxiliaire de Tolerie et de Mecanique

[21] Appl. No.: 444,156

[22] Filed: Jan. 2, 1990

[30] Foreign Application Priority Data

Mar. 2, 1988 [FR] France ............................. 88 02974

[51] Int. Cl.$^5$ ............................................ G01T 1/166
[52] U.S. Cl. ......................... 250/363.05; 250/363.02; 250/363.04; 250/363.08
[58] Field of Search ..................... 250/363.05, 363.08, 250/363.04, 363.02; 248/913

[56] References Cited

U.S. PATENT DOCUMENTS

| | | | |
|---|---|---|---|
| 3,870,886 | 3/1975 | Casale | 250/367 |
| 4,220,861 | 9/1980 | Colombo et al. | 250/363.05 |
| 4,550,623 | 11/1988 | Gysling | 74/89.2 |
| 4,651,007 | 3/1987 | Perusek et al. | 250/363.08 |
| 4,652,759 | 3/1987 | Platz | 250/363.05 |
| 4,781,067 | 11/1988 | Cichanski | 73/620 |

FOREIGN PATENT DOCUMENTS 1284103 7/1962 France .
2398937 2/1979 France .
2593258 2/1986 France .

*Primary Examiner*—Constantine Hannaher
*Attorney, Agent, or Firm*—Charles Berman

[57] ABSTRACT

The invention involves devices for moving two masses (1, 2) with respect to a central axis of a given center (3) in a direction of movement (4). The device is basically distinguished by the fact that it comprises two sets of slide rails (5, 6) permitting movement in the direction (4), mechanisms for mounting each of the two masses on the slide rails so that they can move symmetrically with respect to the point (3), two traction bands (16, 17) that can move in any direction making an angle other than a right angle with the direction of movement (4), mechanisms for applying at least one force on each of the two traction bands, mechanisms to link each mass with each of the traction bands, respectively, such that a force applied to one of them permits a force with a component parallel to the direction of movement to be exerted on the corresponding mass. First and second mechanisms (30, 40) transmit in opposite directions the forces applied to a first traction band to a second traction band and vice versa. This is particularly suitable for the construction of a tomography device.

20 Claims, 1 Drawing Sheet

DEVICE FOR MOVING AT LEAST TWO MASSES WITH RESPECT TO A CENTRAL AXIS OF SYMMETRY

This application is a continuing application of International Application PCT/FR 89/00080 filed internationally on Mar. 1, 1989 and filed in the U.S. PCT office in the national phase on Nov. 1, 1989, and subsequently granted a filing date of Jan. 2, 1990, contents of which are incorporated by reference herein.

BACKGROUND

This invention involves devices for moving at least two masses with respect to a central axis of symmetry in a given direction. In particular, the devices permit the movement on a ring of two cameras for tomographic scanning of the body of a patient, for example.

There already exists a technique called tomography that basically permits the formation of an image, layer by layer, of a given body by means of cameras adapted, for example, from those used for X-rays or the like. Very simplistically, a tomographic scanner (CAT scanner) comprises a frame, sometimes mounted on rails, with a central opening into which a bed on which a patient is lying can be moved. On this frame is usually mounted a rotating plate supporting two components permitting the formation of images, as described above. These two components are usually two cameras arranged symmetrically with respect to the center of the plate and thus to the central opening through which the patients body moves.

For the generation of high-quality images of the internal organs of the patient, it is necessary, for the essential purpose of accommodating and focusing the optical components, to move the two cameras symmetrically with respect to the axis of the turning plate. However, the cameras used in the technique of tomography, on the one hand, are relatively heavy and, on the other hand, hang over the plate, since the patients are in a horizontal position. It is thus conceivable that the movement and maintenance of these overhanging cameras pose technical problems that are relatively difficult to solve, in light of the fact that to obtain clear images, it is necessary that these cameras be positioned perfectly with respect to the center of symmetry and that they move as precisely as possible, specifically, without any play and without being subject to parasite vibrations.

SUMMARY

The invention is for a device for moving two masses with respect to a central axis of symmetry in a given direction such that the two masses move simultaneously in the same amplitude but in opposite directions, of simple construction, taking up a minimum of space, and consuming very little energy during operation.

More specifically, the invention covers a device for moving two masses with respect to a central axis of symmetry with a given center in a first given direction, distinguished by the fact that it comprises:

two sets of slide rails arranged symmetrically with respect to said central point, each set of slide rails permitting movement in said first direction, mechanisms for moving each of the two masses on each of the two sets of slide rails, respectively, such that each of them can move with respect to said central point, two traction bands oriented in a second direction forming an angle other than a right angle with the first direction, both of said bands being symmetrical with respect to said central point and capable of moving in said second direction, mechanisms for applying at least one force to one of the two said traction bands, mechanisms to link each mass to each traction band, respectively, such that a force applied to one of said bands permits a force with a component parallel to said first direction to be exerted on the mass, first mechanisms to transmit forces applied to the end of a first traction band farther from said center of symmetry to the end of the other, second band closer to said center, and second mechanisms to transmit forces applied to the end of said first band closer to the center to the end of said second band farther from said center.

Other aspects and advantages of this invention will become apparent during the course of the following description, related to the drawings attached for illustrative but not limiting purposes.

DRAWINGS

Figure 2:
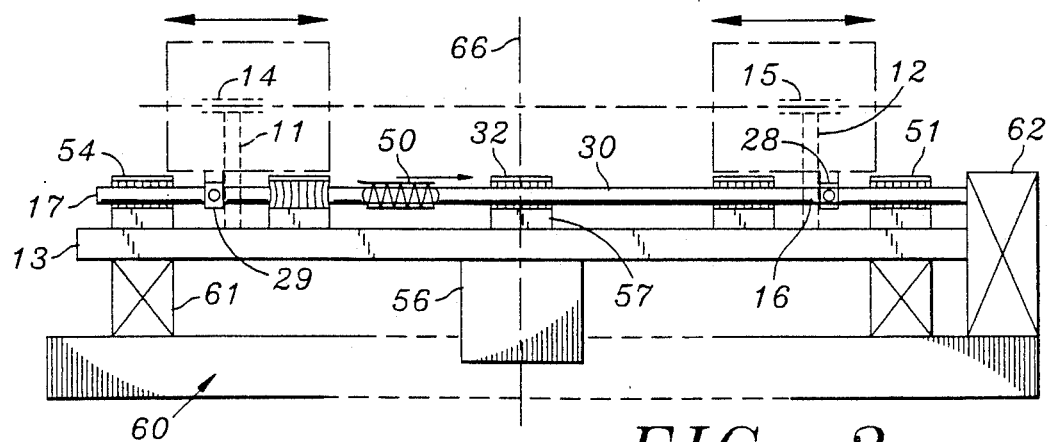

FIGS. 1 and 2 show a front and side view, respectively, of one version of the device covered by this application, specifically adapted to a two-camera CAT scanner.

DESCRIPTION

The two figures show a version of a device permitting the symmetrical movement of two masses (1, 2) with respect to a central point (3) in a given direction of movement (4).

The device comprises two sets of slide rails (5, 6) arranged symmetrically with respect to the center (3) that permit the masses to move in the direction of movement (4) and mechanisms for mounting the two masses (1, 2) on the two sets of slide rails (5, 6), respectively, such that each of the two masses can move with respect to the center (3).

For example, these slide rails could consist of two cylindrical rods (7-8, 9-10), mounted on legs (11, 12, etc.) attached to a baseplate (13). As for mechanisms to connect these two masses to these rods, they could consist of coupling sleeves (14, 15, etc.) connected to the two masses (1, 2) surrounding the two rods by means of bearings, such as needle bearings, so as to be able to slide on them without play.

The device also includes two traction bands (16, 17), symmetrical with respect to the central point (3) and oriented in a second direction forming an angle other than a right angle with the direction of movement (4). These bands are associated with mechanisms (18, 19) permitting them to move in this second direction. In a version that has advantages with respect to construction of the device and the distribution of tensile strength, as explained below, this second direction is parallel to the direction of movement (4).

One advantageous version of the device covered by this application features mechanisms to applying at least one force to one of the two traction bands (16, 17). This force must be transmitted to the masses, and for this purpose the device incorporates mechanisms (28, 29) each connecting one mass (1, 2) to one of the two traction bands (16, 17) in such a way that a force applied to one band permits a force with a component parallel to the direction of movement (4) to be exerted on the mass to which the band is connected. These mechanisms (28, 29) could, for example, consist of legs attached to the two masses, respectively, at one end and gripping the two traction bands (16, 17) at the other.

The device also features first mechanisms (30) to transmit the forces applied to the end (20) of a first traction band (16) farther from the center of symmetry (3) to the end (21) of the other band (17) closer to the center (3), and second mechanisms (40) to transmit the forces applied to the end (22) of the band (16) closer to the center (3) to the end (23) of the band (17) farther from this center.

In one advantageous version of the invention, the first (30) and second (40) mechanisms consist, respectively, of two linking bands (31, 41), a first linking band (31) connecting to the end (20) of the traction band (16) farther from the center (3) to the end (21) of the traction band (17) closer to the center and a second linking band (41) connecting to the end (23) of the traction band (17) farther from this center, each of these two linking bands (31, 41) respectively moving in concert with two sheave pulleys (32, 42) through which they pass.

As mentioned above, the device features four bands, each with a well-defined function, but connected to one another consecutively. These bands can also be designed as a single band that forms a closed loop. In this case, since this loop moves in concert with the pulleys and must remain in continuous contact with them, a tension device (50) is inserted in the loop.

As mentioned before, the two traction bands (16, 17) are associated with mechanisms (18, 19) that permit them to be moved in a second direction that will be, as explained later in the description of the device and as illustrated, identical to the direction of movement (5). Further, since the bands are arranged in a loop guided by pulleys, the mechanisms (18, 19) can respectively be comprised of two pairs of pulleys (51-52, 53-54) arranged symmetrically with respect to the center of symmetry (3), the two pulleys in each pair being exteriorly tangent to a right angle to the direction of movement (4) passing through the center of symmetry (3).

This arrangement of the bands in a single loop offers an advantage for the construction of mechanisms permitting the application of a tensile force to one of the traction bands (16, 17). These mechanisms can thus consist of a drive motor (50) the axis of the output (57) of which is connected to only one of the pulleys, for example, pulley 32, passed and pressed by linking band (31) which forms a portion of the closed loop. Since the loop is closed and exerts pressure on the other pulley by means of gearing, for example, the driving of a single one permits the entire loop to move over a given distance, as explained below in the operating description.

The bands mentioned earlier may be of various type strap, belt, chain, etc. The drive may be provided by any adapted technique—friction, gearing, etc.

Of course, in the case of a tomographic application, the two masses (1, 2) are cameras, for example, and the baseplate (13) supporting all the mechanisms described above will be connected to a frame (60) by any means, especially slide rails (61) permitting the pivoting of the baseplate (13) around an axis (66) passing through the center of symmetry (3). The rotation of this baseplate (13) can be handled by a motor (62) connected to the frame (60), the mechanisms of the drive output of which are connected to the baseplate (13) in order to cause this to rotate around the axis (66) As described above, the baseplate (13) is arranged in a vertical plane in association with the frame (60) so as to position its central opening (63) at a level that permits the bed (64) of a patient (65) to pass through the interior of the frame. These various components and their arrangement, already well known, will not be described any further here. Of course, the traction and linking bands form the closed loop, and the sheave and drive pulleys are arranged so as to leave the opening (63) of the baseplate (13) entirely unencumbered.

The operation of the device described above is detailed hereafter for the case of a CAT scanner in which the two masses (1, 2) consist of cameras attached respectively to their slide rails (5, 6). The closed loop of the various bands is positioned on the various drive and/or sheave pulleys, and the two cameras are connected to this single band so as to be symmetrical with respect to the center of symmetry (3)

In this case, if the cameras have the same mass, which is usually the case, the force exerted by the mass of this camera on the traction band (16)—that is, the weight of this camera 1—is transferred to the second traction band (17) by the linking band (31). Likewise, the weight of camera 2 applied to the second traction band (17) is transferred to the first traction band (16) by means of the second linking band (41).

Since the cameras are initially arranged symmetrically with respect to the central point (3), they are held laterally by slide rails, and their masses are assumed to be identical, these two cameras are held in position by the opposite tensile forces transferred by the various bands.

In contrast, if it is desired to move the two cameras (1, 2) symmetrically with respect to the central point (3), it suffices to drive, by means of the motor (56), just one of the pulleys, in this case pulley 32, which in turn drives the loop band and, thanks to the configuration described above, moves the camera linking points of this loop band symmetrically with respect to the central point (3), thus permitting the desired symmetrical movement of the two cameras, whether farther apart or closer together, to be obtained.

This configuration incontestably provides at least the following two advantages: the fact that the movement of the two cameras can be achieved with a minimum of energy because the only forces to be overcome are the friction of the bands on the pulleys and the sleeves (14, 15) on the rods (7-10), since the tract forces transmitted by the bands balance out. Also, the force that transfers via the bands, especially via the linking bands (31 arid 41), permits the freeing of the central opening (63), of the baseplate (13). This facilitates the passage of the patient lying abed, while at the same time taking up a minimum of space. Of course, it is possible to extend the device described above to the movement of many masses or cameras.

We claim:

1. A device for moving two masses (1, 2) with respect to a given central axis of symmetry (3) in a given first direction of movement (4), comprising:

two sets of slide rails (5, 6) arranged symmetrically with respect to said central axis, each set of slide rails permitting movement in said first direction, mechanisms (14, 15) for mounting the two masses on the two sets of slide rails, respectively, such that each of the two masses may move with respect to the central point (3), two traction bands (16, 17) oriented in a second direction forming an angle other than a right angle with said first direction (4), symmetrically with respect to said central point (3), both traction bands being movable in said second direction, mechanisms (56, 57) for applying at least one force to one of the two said traction bands, mechanisms (28, 29) to connect each mass (1, 2) to one of said traction bands (16, 17), respectively, in such a way that a force applied to one of said bands permits a force with a component parallel to said first direction (4) to be exerted on the mass to which it is connected, first mechanisms (30) to transmit forces applied to the end (20) of a first traction band (16) farther from said central point (3) to the end (21) of the other, second band (17) closer to said point, and second mechanisms (40) to transmit forces applied to the end (22) of said first band (16) closer to said central point to the end (23) of said second band (17) farther from said point.

2. A device as in claim 1, wherein said first and second mechanisms are comprised of two linking bands (31, 41), the first linking band (31) connecting the end (20) of a first traction band (16) farther from said central point (3) to the end (21) of said second traction band (17) closer to said central point and the second linking band (41) connecting the end (23) of the first traction band (16) closer to said central point to the end (23) of said second traction band (17) farther from said central point, and sheave pulleys (32, 42) whereby they are able to coordinate the movements of the two said first and second linking bands.

3. A device as in claim 2, wherein the two said traction bands (16, 17) and the two said linking band (31, 41) form a closed loop.

4. A device as in claim 3, including a tension device (50) in inserted in said closed loop.

5. A device as claimed in claim 4 wherein the two traction bands (16, 17) are mounted to move in a coordinated manner on two pairs of pulleys (51-52, 53-54), respectively, arranged symmetrically with respect to said central point (3), the two pulleys of a given pair being exteriorly tangent to a right angle to the direction of movement (4) passing through said point (3).

6. A device as claimed in claim 4, including said mechanisms or applying at least one force to one of the two said traction bands are comprised of a drive motor (56) the axis (57) of which is connected to at least one of the sheave pulleys (32, 42) that moves in concert with said closed loop.

7. A device as claimed in claim 3, including said mechanisms for applying at least one force to one of the two said traction bands are comprised of a drive motor (56) the axis (57) of which is connected to at least one of the sheave pulleys (32, 42) that moves in concert with said closed loop.

8. A device as claimed in claim 3 wherein the two traction bands (16, 17) are mounted to move in a coordinated manner on two pairs of pulleys (51-52, 53-54), respectively, arranged symmetrically with respect to said central point (3), the two pulleys of a given pair being exteriorly tangent to a right angle to the direction of movement (4) passing through said point (3).

9. A device as claimed in claim 2 wherein the two traction bands (16, 17) are mounted to move in a coordinated manner on two pairs of pulleys (51-52, 53-54), respectively, arranged symmetrically with respect to said central point (3), the two pulleys of a given pair being exteriorly tangent to a right angle to the direction of movement (4) passing through said point (3).

10. A device as claimed in claim 1 wherein the two traction bands (16, 17) are mounted to move in a coordinated manner on two pairs of pulleys (51-52, 53-54), respectively, arranged symmetrically with respect to said central point (3), the two pulleys of a given pair being exteriorly tangent to a right angle to the direction of movement (4) passing through said point (3).

11. A CAT scanner featuring two cameras (1, 2) moving with respect to a given center of symmetry (3) in a first direction of movement (4), comprising:

a baseplate (13) including a central opening (63) centered on said central point, two sets of slide rails (5, 6) arranged symmetrically with respect to said central point (3) on said baseplate (13), each set of slide rails permitting movement in said first direction (4), mechanisms (14, 15) for mounting each of the two cameras on each set of slide rails, respectively, such that each of the two cameras can move with respect to said central point, two traction bands (16, 17) oriented in a second direction forming an angle other than a right angle with the first direction, symmetrically with respect to said central point (3), said traction bands being able to move in said second direction, mechanisms (56, 57) for applying at least one force to one of the two traction bands (16, 17), mechanisms (28, 29) to connect each camera with each of said traction bands, respectively, in such a way that a force applied to one of the traction bands permits a force with a component parallel to said first direction (4) to be exerted on the camera to which it is connected, first mechanisms (30) to transmit forces applied to the end (20) of a first traction band (16) farther from said central point (3) to the end (21) of the other, second traction band (17) farther from said point, and second mechanisms (40) to transmit forces applied to the end (22) of said second traction band (16) closer to said central point to the end (23) of the said second band (17) farther from said point.

12. A device as in claim 11, wherein said first (30) and second (40) mechanisms are comprised of two linking bands (31, 41), the first linking band (31) connecting the end of a first traction band farther from said central point to the end of said second traction band closer to said central point and the second linking band (41) connecting the end of the first traction band closer to said central point to the end of said second traction band farther from said central point, and sheave pulleys (32, 42), mounted to turn on said baseplate (13) clear of said central opening, that are able to coordinate the movement, of said first and second linking bands to both guide and drive them.

13. A device as in claim 12, wherein the two said traction bands and the two said linking bands form a closed loop enclosing said central opening.

14. A device as in claim 13, including a tension device (50) is inserted in said closed loop.

15. A device as claimed in claim 14 wherein the two traction bands (16, 17) are mounted to move in concert on two pairs of pulleys (51-52, 53-54), respectively, arranged symmetrically with respect to the central point (3), both pulleys of a given pair being exteriorly tangent to a right angle parallel to said first direction (4) passing through said central point.

16. A device as claimed in claim 14 wherein said mechanisms for applying at least one force to one of the two traction bands are comprised of a drive motor (56) connected to said baseplate, the axis (57) of which is connected to at least one (32, 42) of the sheave pulleys that moves in concert with said closed loop.

17. A device as claimed in claim 13 wherein said mechanisms for applying at least one force to one of the two traction bands are comprised of a drive motor (56) connected to said baseplate, the axis (57) of which is connected to at least one (32, 42) of the sheave pulleys that moves in concert with said closed loop.

18. A device as claimed in claim 13 wherein the two traction bands (16, 17) are mounted to move in concert on two pairs of pulleys (51-52, 53-54), respectively, arranged symmetrically with respect to the central point (3), both pulleys of a given pair being exteriorly tangent to a right angle parallel to said first direction (4) passing through said central point.

19. A device as claimed in claim 12 wherein the two traction bands (16, 17) are mounted to move in concert on two pairs of pulleys (51-52, 53-54), respectively, arranged symmetrically with respect to the central point (3), both pulleys of a given pair being exteriorly tangent to a right angle parallel to said first direction (4) passing through said central point.

20. A device as claimed in claim 11 wherein the two traction bands (16, 17) are mounted to move in concert on two pairs of pulleys (51-52, 53-54), respectively, arranged symmetrically with respect to the central point (3), both pulleys of a given pair being exteriorly tangent to a right angle parallel to said first direction (4) passing through said central point.

* * * * *